United States Patent [19]
Urban

[11] Patent Number: 5,998,623
[45] Date of Patent: Dec. 7, 1999

[54] PROCESS AND INTERMEDIATES FOR PREPARING 4'-TRIFLUOROMETHYLBIPHENYL-2-CARBOXYLIC ACID [2-(2H-[1,2,4]TRIAZOL-3-YLMETHYL)-1,2,3,4-TETRAHYDRO-ISOQUINOLIN-6-YL]-AMIDE

[75] Inventor: Frank John Urban, Waterford, Conn.

[73] Assignee: Pfizer Inc., New York, N.Y.

[21] Appl. No.: 09/147,197

[22] PCT Filed: Mar. 13, 1997

[86] PCT No.: PCT/IB97/00254

§ 371 Date: Oct. 28, 1998

§ 102(e) Date: Oct. 28, 1998

[87] PCT Pub. No.: WO97/41111

PCT Pub. Date: Nov. 6, 1997

Related U.S. Application Data

[60] Provisional application No. 60/016,495, Apr. 30, 1996.

[51] Int. Cl.⁶ .................................................. C07D 401/06
[52] U.S. Cl. ............................................. 546/143; 546/148
[58] Field of Search ...................................... 546/143, 148

[56] References Cited

FOREIGN PATENT DOCUMENTS

| | | |
|---|---|---|
| 584446 | 3/1994 | European Pat. Off. . |
| 635492 | 1/1995 | European Pat. Off. . |
| 643057 | 3/1995 | European Pat. Off. . |
| WO 96 40640 | 12/1996 | WIPO . |

*Primary Examiner*—Bernard Dentz
*Attorney, Agent, or Firm*—Peter C. Richardson; Gregg C. Benson; Mervin E. Brokke

[57] ABSTRACT

A process for preparing the compound of formula (1) is disclosed.

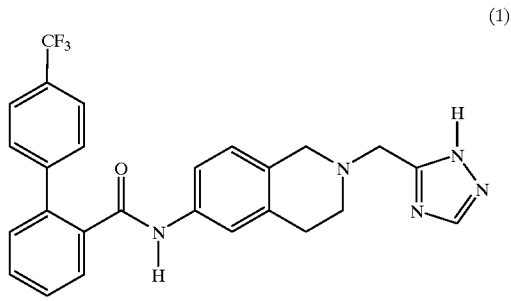

(1)

The starting materials are an N-triazolylmethyl-6-aminoisoquinoline and a 4-biphenyl-2-carboxylic acid derivative.

13 Claims, No Drawings

PROCESS AND INTERMEDIATES FOR PREPARING 4'-TRIFLUOROMETHYLBIPHENYL-2-CARBOXYLIC ACID [2-(2H-[1,2,4]TRIAZOL-3-YLMETHYL)-1,2,3,4-TETRAHYDRO-ISOQUINOLIN-6-YL]-AMIDE

This application is a 371 of PCT/IB97/00254, filed Mar. 13, 1997 as a continuation of United States provisional application 60/016,495, filed Apr. 30, 1996.

FIELD OF THE INVENTION

This invention relates to 4'-trifluoromethylbiphenyl-2-carboxylic acid [2-(2H-[1,2,4]triazol-3-ylmethyl)-1,2,3,4-tetrahydro-isoquinolin-6-yl]-amide of formula I below. More particularly it relates to an improved method, and intermediates, for the preparation of compound I. Compound I is an inhibitor of microsomal triglyceride transfer protein C and/or apolipoprotein B (Apo B) secretion and is, accordingly, useful for the prevention and treatment of atherosclerosis and its clinical sequelae, for lowering serum lipids, and related diseases.

BACKGROUND OF THE INVENTION

Microsomal triglyceride transfer protein (MTP) catalyzes the transport of triglyceride, cholesteryl ester, and phospholipids. It has been implicated as a probable agent in the assembly of Apo B-containing lipoproteins, biomolecules which contribute to the formation of atherosclerotic lesions. See European Patent application publication no. 0 643 057 A1, European Patent application publication no. 0 584 446 A2, and Wetterau et al., Science, 258, 999–1001, (1992). Compounds which inhibit MTP and/or otherwise inhibit Apo B secretion are, therefore, useful in the treatment of atherosclerosis. Such compounds are also useful in the treatment of other diseases or conditions in which, by inhibiting MTP and/or Apo B secretion, serum cholesterol and triglyceride levels can be reduced. Such conditions include hypercholesterolemia, hypertriglyceridemia, pancreatitis, and obesity; and hypercholesterolemia, hypertriglyceridemia, and hyperlipidemia associated with pancreatitis, obesity, and diabetes.

SUMMARY OF THE INVENTION

This invention provides a method for preparing the compound of formula

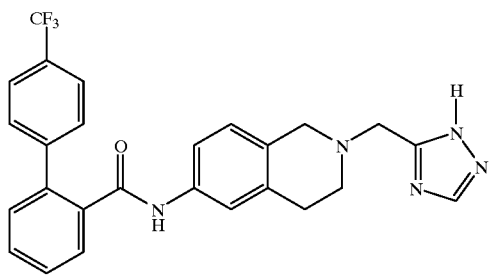

I which comprises treating the compound of the formula

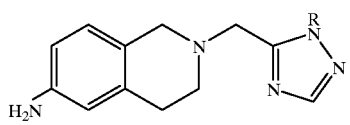

III wherein R is H or $R^2$ and $R^2$ is selected from allyl and a substituted methyl group wherein the substituents comprise one to three ($C_6$–$C_{10}$)aryl groups wherein the aryl groups are optionally substituted with one or more substituents selected from nitro and ($C_1$–$C_6$)alkoxy;

a) with a compound of the formula

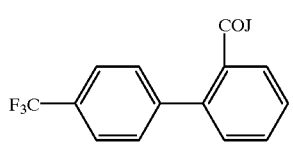

X wherein J is a leaving group such as a halogen atom, an azido group, a ($C_1$–$C_6$)acyloxy group or a ($C_6$–$C_{10}$) aroyloxy group, preferably a chlorine or bromine atom; and b) when R is $R^2$ further treating the product of step a) with an acid such as trifluoroacetic acid (TFA), p-toluenesulfonic acid (PTSA), methane- or trifluoromethanesulfonic acid and HBr in acetic acid, preferably trifluoroacetic acid.

Reference to a moiety as "heterocyclic" means any single ring or fused ring system containing at least one ring heteroatom independently selected from O, N, and S. Thus a polycyclic fused ring system containing one or more carbocyclic fused saturated, partially unsaturated, or aromatic rings (usually benzene rings) is within the definition of heterocyclyl so long as the system also contains at least one fused ring which contains at least one of the aforementioned heteroatoms. As a substituent, such heterocyclic rings may be attached to the remainder of the molecule from either a carbocyclic (e.g., benzene) ring or from a heterocyclic ring.

Reference to a moiety containing "one or more rings" is intended to mean that said moiety contains a single or fused cyclic moiety or moieties. The rings may be carbocyclic or heterocyclic, saturated or partially unsaturated, and aromatic or non-aromatic.

Reference to a fused polycyclic ring system or radical means that all rings in the system are fused.

Reference to "halo" in this specification is inclusive of fluoro, chloro, bromo, and iodo unless noted otherwise.

Reference to an "aryl" substitutent (e.g. ($C_6$–$C_{10}$)aryl) means the ring or substitutent is carbocyclic. Aromatic moieties which contain one or more heteroatoms are included as a subset of the term "heterocyclic", as discussed above.

Reference to an "acyl" substituent refers to an aliphatic or cyclic hydrocarbon moiety attached to a carbonyl group through which the substituent bonds.

Reference to "alkyl" and "alkoxy" include both straight and, when the moiety contains more than two carbon atoms, branched of cyclic chain radicals, but it is to be understood that references to individual radicals such as "propyl" or "propoxy" embrace only the straight chain ("normal") radical, branched chain isomers such as "isopropyl" or "isopropoxy" being referred to specifically.

Certain intermediates of the formula

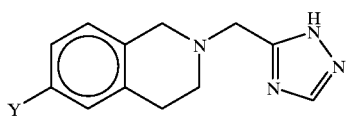

and their tautomers, wherein Y is $NH_2$ or $NO_2$, are additionally provided as a further feature of the invention. One skilled in the art will understand that the above compounds may exist in several tautomeric forms all of which are included in the invention. Another intermediate provided by the invention is the compound of the formula

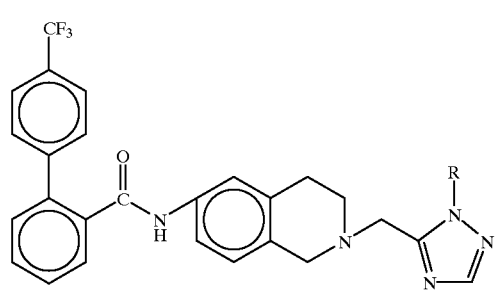

II wherein R is $R^2$, preferably $CH_3OC_6H_4CH_2$—.

DETAILED DESCRIPTION OF THE INVENTION

In the reaction Schemes and description which follow R, $R^2$, J, K and Y as well as structural formulae I through X are as defined above.

SCHEME 1

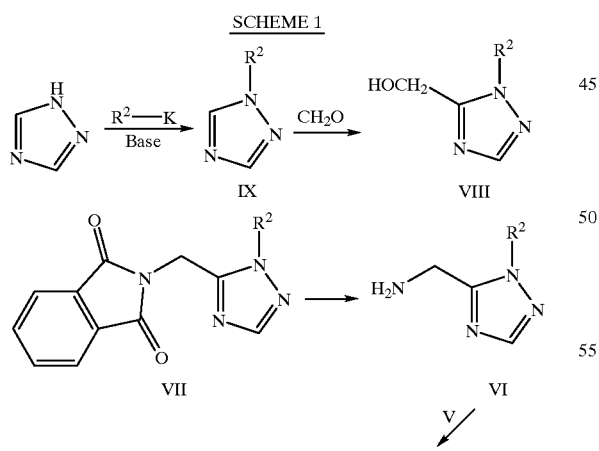

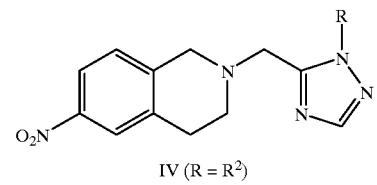

IV (R = $R^2$)

SCHEME 2

IV (R = $R^2$)

↓ TFA

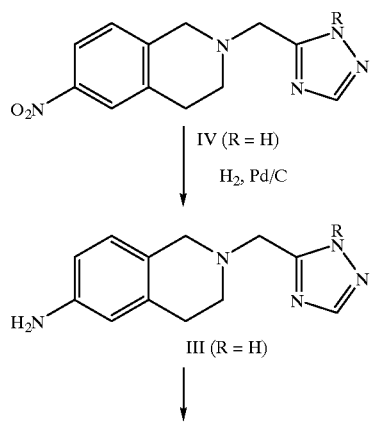

I

SCHEME 3

IV (R = $R^2$)

↓ $H_2$, Pd/C          Pd/C

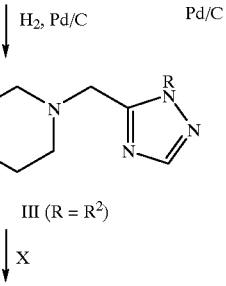

III (R = $R^2$)

↓ X

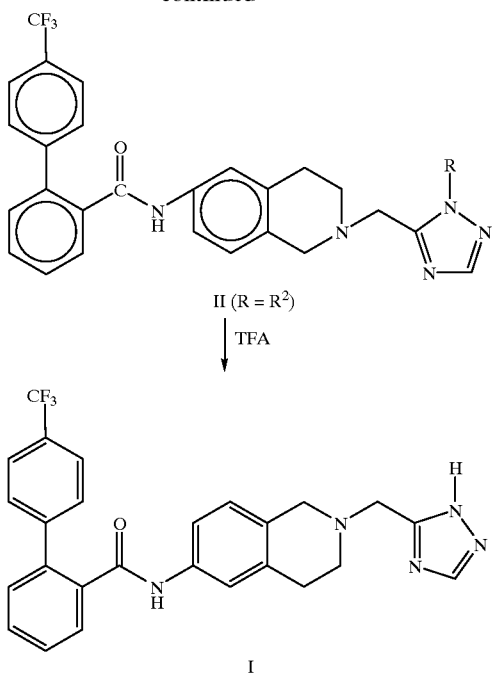

II (R = R²)

↓ TFA

I

As shown in Scheme 1 compound IX is prepared by reacting 1,2,4-triazole with a compound of the formula R²K wherein K, is halo as defined above, in the presence of a base. Preferably R²K is 4-methoxybenzyl chloride. The reaction is carried out at about room temperature in a polar solvent such as a N,N,-di($C_1$–$C_6$)alkylcarboxamide, e.g., dimethylacetamide (DMAC) and dimethylformamide (DMF); a ketone, e.g., acetone and methylethylketone; a ($C_1$–$C_6$)alkanol, e.g., ethanol, methanol and isopropanol; and mixtures thereof. Bases useful in the practice of this aspect of the invention include alkali metal hydroxides, carbonates and hydrogen carbonates. Preferably the solvent is DMF and the base is NaOH.

Compound VIII is prepared by heating compound IX with formaldehyde in hot water. The reaction is affected at reflux temperature using an external heat source at from about 100 to about 135° C. The formaldehyde, which is used in excess, can be supplied in the form of its 37% aqueous solution (also known as formalin) or its linear polymeric (paraformaldehyde) and trimeric (trioxane) forms. Paraformaldehyde decomposes in hot water, and trioxane in aqueous solutions containing strong acids, to yield formaldehyde. The preferred source of formaldehyde is formalin.

Compound VII is formed by treating compound VIII, in a Mitsunobu reaction, with phthalimide in the presence of triphenylphosphine and a di($C_1$–$C_6$)alkyl or dipiperidinyl azodicarboxylate. The preferred azodicarboxylate is the diisopropyl ester. The reaction may be effected at a temperature of from about 0 to about 65° C. in an aprotic solvent such as tetrahydrofuran (THF), isopropyl ether and dioxane. Preferably the reaction is carried out at about 15° C. in THF.

Compound VII is converted to compound VI by suspension in an aprotic suspension medium such as a ($C_1$–$C_6$) alkanol, e.g., methanol, ethanol or isopropanol, and treatment with hydrazine. The hydrazine is preferably provided in the form of its hydrate and the preferred suspension medium is methanol. The reaction can be effected at a temperature of about room temperature to about 65° C., preferably room temperature.

Compound IV, (R=R²), is formed by treatment of compound VI with

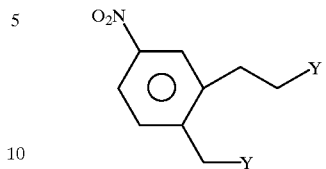

V wherein Y is selected from halo and optionally substituted ($C_1$–$C_6$)alkyl- or ($C_1$–$C_6$)arysulfonoxy groups, in the presence of a base and an aprotic solvent. Preferably $CH_3SO_3$ (mesyloxy). The reaction is effected under an inert atmosphere, such as nitrogen or argon, at a temperature of about ambient to the reflux temperature of the solvent. The bases which may be used are organic bases such as tri ($C_1$–$C_6$)alkylamines, pyridine and N-methylmorpholine. Aprotic solvents include THF, $CH_2Cl_2$ and DMF. The reaction is preferably effected in THF, under nitrogen, at the reflux temperature of the solvent. The preferred base is triethylamine. Compound V, wherein Y is mesyloxy, may be prepared by treating a suspension of compound V wherein Y is OH in a ($C_1$–$C_6$)haloalkane, at a low temperature under an inert atmosphere, with mesyl chloride in the presence of a base. Bases useful in the practice of this aspect can be selected from those described above. The inert atmospheres may be selected from those described above. The temperature is from about −40 to about 0° C. The reaction is preferably carried out under nitrogen, at about −30° C. in the presence of triethylamine.

As shown in Scheme 3 compound IV (R=R²) is converted to compound IV (R=H) by treatment with an acid such as trifluoroacetic acid (TFA), p-toluenesulfonic acid, methane or trifluoromethanesulfonic acid and HBr in acetic acid, preferably trifluoroacetic acid. The reaction may be carried out at a temperature from about room temperature to about 60° C. preferably at room temperature. The TFA may be used neat or dissolved in $CH_2Cl_2$.

Compound IV, wherein R is hydrogen, is converted to compound III, wherein R is hydrogen, by treatment with hydrogen, at a pressure of from about 1 to about 3 Atom in the presence of a hydrogenation catalyst and an organic solvent. Hydrogenation catalysts include Pd, Pt and Raney Ni. The metals may be used in the form of salts, e.g., $Pd(OH)_2$, or on carriers, e.g., carbon. The hydrogenation is effected at a temperature from about room temperature to about 50° C., preferably at room temperature. The preferred hydrogenation catalyst is 10% Pd/C and the preferred solvent is methanol.

Compound III wherein R is hydrogen, is converted to compound I by treatment with a source of the 4'-trifluoromethylbiphenyl-2-carbonyl group selected from the halides, azides and mixed anhydrides, in the presence of a solvent and a base. The reaction is effected at a temperature from about room temperature to about 50° C. preferably at room temperature. Solvents useful in aspect of the invention include aprotic solvents, as described above, haloalkanes and mixtures thereof. A preferred solvent is the mixture of THF and methylene chloride which is formed when a solution of the carbonyl compound, in methylene chloride, is added to a suspension of compound III (R=H) in THF.

Alternatively, as shown in Scheme 3, compound I can be prepared by treating compound III wherein R is R² with a 4'-trifluoromethylbiphenyl-2-carbonyl source, as described above, to form the compound of formula II and treating compound II with an acid such as trifluoroacetic acid (TFA), p-toluenesulfonic acid, methane or trifluoromethanesulfonic acid and HBr in acetic acid, preferably trifluoroacetic acid as described above. Preferably, $R^2$ is p-$CH_3OC_6H_4CH_2$— and the 4'-trifluoromethylbiphenyl-2-carbonyl source is the chloride.

The compound of formula I and its tautomers form acid addition salts and the expression "pharmaceutically-acceptable salts" is intended to include but not is to be limited to such salts as the hydrochloride, hydrobromide, sulfate, hydrogen sulfate, phosphate, hydrogen phosphate, dihydrogenphosphate, acetate, succinate, citrate, methanesulfonate and p-toluenesulfonate salts. It can also form polyaddition salts.

The acid addition salts of the compound of formula I, and its tautomers, are readily prepared by reacting the base form with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The compound of formula I, its tautomers, and their pharmaceutically acceptable acid salts, (hereafter 'the active compounds") are orally administrable and are accordingly used in combination with a pharmaceutically acceptable carrier or diluent suitable to oral dosage forms. Suitable pharmaceutically-acceptable carriers include inert solid fillers or diluents and sterile aqueous or organic solutions. The active compounds will be present in such pharmaceutical compositions in amounts sufficient to provide the desired dosage amount in the range described below. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. Pharmaceutical compositions comprising the active compounds are suitable for the treatment of conditions including atherosclerosis, pancreatitis, obesity, hypercholesterolemia, hypertriglyceridemia, hyperlipidemia, and diabetes, comprising a compound of formula I as hereinbefore defined, and a pharmaceutically acceptable carrier.

The active compounds inhibit or decrease apo B secretion, likely by the inhibition of MTP, although it may be possible that other mechanisms are involved as well. The compounds are useful in any of the diseases or conditions in which apo B, serum cholesterol, and/or triglyceride levels are elevated. Accordingly, the invention further provides a method of treating a condition selected from atherosclerosis, pancreatitis, obesity, hypercholesteremia, hypertriglyceridemia, hyperlipidemia, and diabetes, comprising administering to a mammal, especially a human, in need of such treatment an amount of a compound of formula I as defined above sufficient to decrease the secretion of apolipoprotein B. A subgroup of the preceding conditions includes atherosclerosis, obesity, pancreatitis, and diabetes. A more particular subgroup includes atherosclerosis.

The term "treating" as used herein with respect to the active compounds includes preventative as well as disease remitative treatment.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The active compounds may also be administered parenterally. For parenteral administration the compounds can be combined with sterile aqueous or organic media to form injectable solutions or suspensions. Solutions or suspensions of these active compounds can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The dose of an active compound which is administered will generally be varied according to principles well known in the art taking into account the severity of the condition being treated and the route of administration. In general, the active compound will be administered to a warm blooded animal (such as a human) so that an effective dose, usually a daily dose administered in unitary or divided portions, is received, for example a dose in the range of about 0.1 to about 15 mg/kg body weight, preferably about 1 to about 5 mg/kg body weight. The total daily dose received will generally be between 1 and 1000 mg, preferably between 5 and 350 mg.

The active compound may be used in conjunction with other pharmaceutical agents, including other lipid lowering agents. Such agents include cholesterol biosynthesis inhibitors, especially HMG CoA reductase inhibitors and squalene synthetase inhibitors; bile acid sequestrants; fibrates; cholesterol absorption inhibitors; and niacin.

A test compound is considered to be active if it is active in any of the following screens.

The activity of an active compound can be assessed by measuring inhibition of apo B secretion in HepG2 cells.

HepG2 cells are grown in Dulbecco's Modified Eagles Medium plus 10% fetal bovine serum (growth medium; Gibco) in 96-well culture plates in a humidified atmosphere containing 5% carbon dioxide until they are approximately 70% confluent. Test compounds are dissolved at 10–20 mM in dimethyl sulfoxide which is then diluted to 1 µM in growth medium. Serial 1:1 dilutions of this stock are made in growth medium and 100 µL of each are added to separate wells of a 96-well culture plates containing HepG2 cells. Twenty four hours later, growth medium is collected and assayed by specific ELISA for apoB and, as a control, apoAI concentrations. Inhibitors are identified as compounds that decrease apoB secretion into the medium without affecting the secretion of apoAI. The ELISA for apoB is performed as follows. Monoclonal antibody against human apoB (Chemicon) is diluted to 5 µg/mL in phosphate buffered saline/azide (PBS+0.02% Na azide) and 100 µL are added to each well of a 96-well plate (NUNC Maxisorb). After an overnight incubation at room temperature, the antibody solution is removed and wells are washed 3 times with PBS/azide. Non-specific sites on the plastic are blocked by incubating wells for 1–3 hours in a solution of 1% (w/v) bovine serum albumin (BSA) made in PBS/azide. 100 µL of various dilutions of growth medium from the HepG2 cells or apoB standards (made in 0.004% Tween 20/1% BSA in PBS/azide) are added to each well and incubated for 18 hours. Wells are aspirated and washed 3 times (0.1% Tween 20 in PBS) prior to adding 100 µL of a 1/1000 dilution of the secondary antibody, goat anti-human apoB (Chemicon). After a 3 hour incubation at room temperature, this solution is aspirated and the wells are again washed 3 times as above. 100 µL of a 1:1600 dilution (in PBS/1% BSA/2 mM $MgCl_2$) of rabbit anti-goat IgG conjugated to alkaline phosphatase (Sigma) are then added to each well and incubated for 1 hour at room temperature. After aspirating, the wells are washed 4 times as above and 100 µL of 1 mg/mL p-nitrophenylphosphate (pNPP; Sigma) in 25 mM sodium bicarbonate 2 mM $MgCl_2$, pH 9.5, are added to each well and incubated for 20–30 minutes and then the reaction is terminated by the addition of 50 µL of 0.2N NaOH. Absorbance of each well is read at 405 nm and the background at 650 nm is subtracted. ApoB concentration is calculated from a standard curve constructed from purified LDL standards that are run in parallel in the same assay. ApoAI is measured in an analogous manner except that antibodies for apoAI (Chemicon) are used in place of the antibodies for apoB and antigen incubation is at 37° instead of room temperature.

Activity can also be confirmed if a test compound inhibits MTP activity directly.

Inhibition of MTP activity by a compound can be measured by observing the inhibition of transfer of radiolabeled triglyceride from donor vesicles to acceptor vesicles in the presence of soluble human MTP. The procedure for preparing MTP is based on the method of Wetterau and Zilversmit (Biochem. Biophys. Acta (1986) 875:610). Briefly, human liver chunks, frozen at −80° C., are thawed on ice, minced, and rinsed several times with ice cold 0.25 M sucrose. All subsequent steps are performed on ice. A 50% homogenate in 0.25 M sucrose is prepared using a Potter-Elvehjem Teflon pestle. The homogenate is diluted 1:1 with 0.25 M sucrose and centrifuged at 10,000×g for 20 minutes at 4° C. The pellet is resuspended in sucrose and recentrifuged at 10,000×g for 20 minutes. The supernatants are combined and the microsomes pelleted by centrifugation at 105,000×g for 75 minutes. The supernatant is discarded and the microsomal pellet is suspended in a minimal volume of 0.25 M sucrose, diluted to 3 mL per gm starting liver weight with 0.15 M Tris-HCl pH 8.0. This suspension is divided into 12 fractions, and centrifuged at 105,000×g for 75 minutes. The supernatants are discarded and the microsomal pellets are stored frozen at −80° C. until needed. For preparation of MTP prior to performing the assay, a thawed pellet is suspended in 12 mL of cold 50 mM Tris-HCl, 50 mM KCl, 5 mM $MgCl_2$], pH 7.4 and 1.2 mL of a 0.54% deoxycholate (pH 7.4) solution is added slowly with mixing to disrupt the microsomal membrane. After a 30 minutes incubation on ice with gentle mixing, the suspension is centrifuged at 105,000×g for 75 minutes. The supernatant, containing the soluble MTP protein, is dialyzed for 2–3 days with 4 changes of assay buffer (150 mM Tris-HCl, 40 mM NaCl, 1 mM EDTA, 0.02% $NaN_3$, pH 7.4). The human liver MTP is stored at 4° C. and diluted 1:5 with assay buffer just before use. MTP preparations show no notable loss of transfer activity with storage up to 30 days.

Liposomes are prepared under nitrogen by room temperature, bath sonication of a dispersion of 400 µM egg phosphatidylcholine (PC), 75 µM bovine heart cardiolipin, and 0.82 µM $^{14}$C-triolein (110 Ci/mol) in assay buffer. The lipids in chloroform are added in the proper amounts and dried under a nitrogen stream before hydrating with assay buffer. Acceptor liposomes are prepared under nitrogen by room temperature bath sonication of a dispersion of 1.2 mM PC, 2.3 µM triolein and 30 pM $^3$H-PC (50 Ci/mol) in assay buffer. The donor and acceptor liposomes are centrifuged at 160,000×g for 2 hours at 7° C. The top 80% of the supernatant, containing small unilamellar liposomes, are carefully removed and stored at 4° C. until used for transfer assays.

MTP activity is measured using a transfer assay which is initiated by mixing donor and acceptor vesicles together with the soluble MTP and test compound. To 100 µL of either a 5% BSA (control) or 5% BSA containing the test compound, are added 500 µL assay buffer, 100 µL donor liposomes, 200 µL acceptor liposomes and 100 µL of diluted MTP protein. After incubation at 37° C. for 45 minutes, triglyceride transfer is terminated by adding 500 µL of a 50% (w/v) DEAE cellulose suspension in assay buffer. Following 4 minutes of agitation, the donor liposomes, bound to the DEAE cellulose, are selectively sedimented by low speed centrifugation. An aliquot of the supernatant containing the acceptor liposomes is counted and the $^3$H and $^{14}$C counts are used to calculate the percent recovery of acceptor liposomes and the percent triglyceride transfer using first order kinetics. Inhibition of triglyceride transfer by test compound is manifested as a decrease in $^{14}$C radioactivity compared to controls where no test compound is present.

Activity of test compounds as MTP inhibitors can also be measured in vivo according to the following test.

Male mice (20–30 g.; various strains) are dosed by oral gavage (0.25 mL/25 g. body weight) with test compound suspended in an aqueous 0.5% methyl cellulose solution. Compound solutions are dosed either multiple times over several days or, alternatively, once 90 minutes before mice are euthanized and blood is collected for preparation of serum. The serum is assayed for triglyceride concentration by a commercial enzymatic assay (Triglyceride G: Wako Fine Chemicals). MTP inhibitors are identified by their ability to lower serum triglycerides as compared to control mice dosed with vehicle.

The present invention is illustrated by the following Examples. However, it should be understood that the invention is not limited to the specific details of these examples.

Conventional methods and/or techniques of purification and separation known to those skilled in the art can be used to isolate the compounds of this invention. Such techniques include all types of chromatography (HPLC, column chromatography using common adsorbents such as silica gel, and thin layer chromatography), recrystallization, and differential (i.e., liquid-liquid) extraction techniques.

PREPARATION 1

1-(4-Methoxybenzyl)-1,2,4-triazole 1,2,4-Triazole (7.5 g, 0.109 mol) was dissolved in dimethylformamide (50 mL) and stirred under a nitrogen atmosphere in an ice bath at 10° C. while partially ground pellets of sodium hydroxide (17.5 g, 0.438 mol) were added in one portion causing an exotherm to about 25° C. A solution of 4-methoxybenzyl chloride (15 mL, 0.111 mol) in DMF was added dropwise over five minutes at 25° C. After stirring at room temperature for four hours, ethyl acetate and water were added. The layers were separated and the aqueous layer was extracted with ethyl acetate. The combined organic layers were washed four times with water and once with brine and dried over magnesium sulfate. The mixture was filtered and the filtrate solvent evaporated in vacuo to afford the title product as an oil in 69% yield; 14.15 g; $^1$H NMR (CDCl$_3$) δ 8.00 (s, 1), 7.93 (s, 1), 7.19 (d, 2), 6.88 (d, 2), 5.23 (s, 2), 3.78 (s, 3). mass spectrum: m/z 109 (M+1).

PREPARATION 2

5-(Hydroxymethyl)-1-(4-methoxybenzyl)-1,2,4-triazole

The title product of Preparation 1 (7.6 g, 40 mmol) was dissolved in 37% aq formaldehyde solution (25 mL) and heated, at reflux, in a 130° C. oil bath for four days. The course of the hydroxymethylation was monitored by TLC on silica gel with 3:1, ethyl acetate:chloroform as eluant. The reaction mixture was cooled to room temperature, poured into water and extracted twice with ethyl acetate. The combined organic layers were washed with 1N NaOH, water and brine. After drying the solution over magnesium sulfate, evaporation afforded a crude product which was slurried in hexanes with a small amount of 2-propanal to yield 4.9 g (56%) of the title product; mp 95–100° C. $^1$H NMR (CDCl$_3$) δ 7.72 (s, 1), 7.21 (d, 2), 6.85 (d, 2), 5.70 (bs, 1, O$\underline{H}$), 5.32 (s, 2), 4.69 (s, 2), 3.78 (s, 3). $^{13}$C NMR (CDCl$_3$) δ 159.6, 149.8, 145.6, 129.2, 127.0, 114.3, 55.3, 54.9, 52.0. IR (KBr) 1610, 1585, 1512 cm$^{-1}$. mass spectrum: m/z 220 (M+1).

Anal. Calcd. for C$_{11}$H$_{13}$N$_3$O$_2$: C, 60.26; H, 5.98; N, 19.17. Found: C, 60.30; H, 6.16; N, 19.66.

The structure was confirmed by single crystal X-ray analysis.

PREPARATION 3

5-(Phthalimidomethyl)-1-(4-methoxybenzyl)-1,2,4-triazole

The title product of Preparation 2 (8.5 g, 38.8 mmol), triphenylphosphine (11.2 g, 42.7 mmol) and phthalimide (6.3 g, 42.7 mmol) were dissolved in tetrahydrofuran (125 mL) at room temperature to provide a cloudy solution. A solution of diisopropyl azodicarboxylate (8.4 mL, 42.7 mmol) in tetrahydrofuran (40 mL) was added, dropwise, over 40 minutes with the temperature being held at about 15° C. with an ice water bath. During the addition the product precipitated as a white solid. The reaction mixture was stirred at room temperature overnight and then was diluted with hexanes (125 mL). After stirring for thirty minutes, the white solid title product was collected, washed with hexanes and dried in vacuo; 12.2 g, 91% yield; mp 167–72° C. $^1$H NMR (CDCl$_3$) δ 7.85 (s, 1), 7.81 (m, 2), 7.69 (m, 2), 7.09 (d, 2), 6.77 (d, 2), 5.43 (s, 2), 4.89 (s, 2), 3.72 (s, 3). $^{13}$C NMR (CDCl$_3$) δ 150.9, 145.6, 134.2, 131.8, 128.3, 127.0, 123.6, 114.3, 112.9, 112.1, 55.2, 52.0, 32.8. IR (KBr) 1772, 1720, 1689, 1612, 1586, 1519 cm$^{-1}$. mass spectrum: m/z 349 (M+1).

Anal. Calcd. for C$_{19}$H$_{16}$N$_4$O$_3$: C, 65.50; H, 4.63; N, 16.08. Found: C, 65.35; H, 4.80; N, 16.18.

PREPARATION 4

5-(Aminomethyl)-1-(4-methoxybenzyl)-1,2,4-triazole

The title product of Preparation 3 (5 g, 14.4 mmol) was suspended in methanol (50 mL) and hydrazine hydrate (1.6 mL, 32 mmol) was added with stirring. After several minutes a clear solution was obtained and the reaction mixture was stirred at room temperature overnight during which time phthaloylhydrazide precipitated. The reaction mixture was diluted with methylene chloride (50 mL) and the slurry of hydrazide was stirred for 45 minutes, filtered and the solids washed with methylene chloride. The filtrate was evaporated in vacuo and the residue was dissolved in methylene chloride and 1NNaOH. The aqueous layer was pH 12. The layers were separated, the aqueous layer was extracted with methylene chloride and the organic layers were combined. After washing the organic layers with brine and drying over magnesium sulfate, the title product was recovered as a colorless oil by evaporation of the solvent in vacuo; 3 g, 97% yield. $^1$H NMR (CDCl$_3$) δ 7.79 (s, 1), 7.12 (d, 2), 6.81 (d, 2), 5.27 (s, 2), 3.88 (s, 2), 3.74 (s, 3), 1.59 (bs, 2, N$\underline{H}_2$). $^{13}$C NMR (CDCl$_3$) δ 150.3, 145.6, 130.4, 129.0, 128.8, 127.3, 114.3, 55.3, 51.7, 37.7.

PREPARATION 5

2-[2-(4-Methoxybenzyl)-2H-[1,2,4]triazol-3-ylmethyl]-6-nitro-1,2,3,4-tetrahydro-isoquinolin 1) 2-(2-Hydroxyethyl)-5-nitrobenzyl alcohol (6.38 g, 32.4 mmol) and triethylamine (11.3 mL, 81 mmol) were suspended in methylene chloride (100 mL), under nitrogen, and cooled to −30° C. with stirring. A solution of methanesulfonyl chloride (5.5 mL, 71.2 mmol) in methylene chloride (32 mL) was added dropwise over fifteen minutes. After thirty minutes, the cooling bath was removed and 1NHCl (130 mL) was added. The mixture was stirred for ten minutes and the layers separated. The organic layer was washed with water, sat. sodium bicarbonate solution and brine. The organic layer was dried over magnesium sulfate and filtered. The filtrate was evaporated in vacuo to provide a yellow solid which was used without further purification; 10.7 g, 94% yield. $^1$H NMR (CDCl$_3$) δ 8.17 (m, 2), 7.66 (d, 1), 5.39 (s, 2), 4.50 (t, 2), 3.28 (t, 2), 3.10 (s, 3), 3.00 (s, 3).

2) The title product of Preparation 4 (1.1 g, 5 mmol) and triethylamine (1.8 mL, 12.7 mmol) were dissolved in tetrahydrofuran (15 mL) under a nitrogen atmosphere and treated dropwise with a solution of the product of step 1) (1.75 g, 5 mmol) in tetrahydrofuran (10 mL). The resulting solution was stirred at room temperature for two hours and at reflux overnight. The reaction mixture was cooled and methylene chloride and 1NNaOH were added. The layers were separated and the aqueous layer was extracted with additional methylene chloride. The combined organic layers were washed with water and brine and dried over magnesium sulfate. The crude product was recovered from the methylene chloride and purified by chromatography over silica gel with 30% ethyl acetate in chloroform; 1.2 g, 63% yield of the title product as a yellow oil which slowly solidified. $^1$H NMR (CDCl$_3$) δ 7.98 (m, 2), 7.88 (s, 1), 7.10 (m, 3), 6.76 (d, 2), 5.40 (s, 2), 3.81 (s, 2), 3.73 (s, 3), 3.63 (s, 2), 2.95 (t, 2), 2.80 (t, 2). $^{13}$C NMR (CDCl$_3$) δ 159.4, 151.4 150.4, 145.6, 141.5, 135.6, 129.0, 127.4, 123.7, 123.7, 120.8, 114.1, 112.1, 55.5, 55.2, 53.1, 52.1, 50.1, 29.0. IR (KBr) 1610, 1584, 1517 cm$^{-1}$. mass spectrum: m/z 380 (M+1).

PREPARATION 6

2-(2H-[1,2,4]triazol-3-ylmethyl)-6-nitro-1,2,3,4-tetrahydro-isoquinoline

The title product of Preparation 5 (8.8 g, 23.2 mmol) was dissolved in trifluoroacetic acid (88 mL) and stirred at room temperature overnight. The reaction mixture was evaporated in vacuo to an oil which was dissolved in methylene chloride. The solution was extracted two times with 1NHCl solution and the combined acidic extracts were washed one time with methylene chloride. The acidic extract was layered with fresh methylene chloride and the pH adjusted to 10 with 10% aq sodium carbonate to precipitate the title product which was collected and washed with water and methylene chloride; 3.99 g, 66% yield; mp 163–6° C. $^1$H NMR (DMSO-d$_6$) δ 8.20 (s, 1), 7.97 (d, 1), 7.92 (dd, 1), 7.30 (s, 1), 3.82 (s, 2), 3.73 (s, 2), 2.92 (t, 2), 2.76 (t, 2). $^{13}$C NMR (DMSO-d$_6$) δ 147.8, 146.2, 143.2, 136.5, 128.2, 123.8, 120.8, 55.1, 53.4, 49.6, 28.9. mass spectrum: m/z 260 (M+1).

Anal. Calcd. for C$_{12}$H$_{13}$N$_5$O$_2$ (0.15 CH$_2$Cl$_2$): C, 53.65; H, 4.93; N, 25.98. Found: C, 53.65; H, 4.93; N, 25.75.

EXAMPLE 1

6-Amino-2-(2H-[1,2,4]triazol-3-ylmethyl)-1,2,3,4-tetrahydroisoquinoline

The title product of Preparation 6 (4.46 g, 17.4 mmol) was dissolved in methanol (220 mL) and hydrogenated over 10% palladium on carbon (2.23 g) at 50 psi (about 345 kPa) for four hours. The catalyst was removed by filtration through Celite® and the methanol in the filtrate was evaporated in vacuo to provide the title product as a white solid, 3.56 g, 91% yield. mp 191–3° C. $^1$H NMR (dimethylsulfoxide-d$_6$) δ 6.65 (d, 1), 6.32 (dd, 1), 6.28 (d, 1), 4.79 (s, 2), 3.71 (s, 2), 3.41 (s, 2), 3.34 (s, 2). $^{13}$C NMR (dimethylsulfoxide-d$_6$) δ 155.9, 147.0, 134.5, 127.1, 122.4, 113.8, 112.7, 55.4, 53.9, 50.9, 29.2. IR (KBr) 1633, 1612, 1584, 1513 cm$^{-1}$. mass spectrum: m/z 230 (M+1).

Anal. Calcd. for C$_{12}$H$_{15}$N$_5$: C, 62.86; H, 6.59; N, 30.55. Found: C, 62.49; H, 6.39; N, 30.45.

EXAMPLE 2

4'-Trifluoromethyl-biphenyl-2-carboxylic acid [2-(2H-[1,2,4]triazol-3-ylmethyl)-1,2,3,4-tetrahydro-isoquinolin-6-yl]-amide (I)

A) The product of Example 1 (3.3 g, 14.5 mmol) was suspended in methylene chloride (100 mL) and tetrahydrofuran (40 mL) with triethylamine (2.23 mL, 15.9 mmol). The suspension was stirred at room temperature while a solution of 4'-trifluoromethylbiphenyl-2-carbonyl chloride (4.13 g, 14.5 mmol) in methylene chloride (40 mL) was added dropwise and the reaction mixture was stirred overnight. Sodium carbonate (17 g, 0.2 mol) in water (440 mL) was added and the mixture stirred for fifteen minutes. The layers were separated and the aqueous layer was extracted a second time with methylene chloride. The combined organic layers were washed with brine, dried over magnesium sulfate and evaporated in vacuo to yield the title product as a foam. This was identical with previous material. $^1$H NMR (CDCl$_3$) δ 13.88 (bs, 1), 10.21 (s, 1), 7.74 (d, 2), 7.67–7.48 (m, 6), 7.31 (s, 1), 7.20 (dd, 1), 6.91 (d, 1), 3.73 (s, 2), 3.56 (s, 2), 2.73 (m, 4). IR (KBr) 1651, 1618, 1603, 1541, 1510 cm$^{-1}$. Mass spectrum: m/z: 478 (M$^+$).

B) The title product of Example 4 (0.49 g, 8.2 mmol) was dissolved in trifluoroacetic acid (5 mL) and stirred at room temperature overnight. The volatiles were removed in vacuo and the residue was dissolved in ethyl acetate and 10% aqueous sodium carbonate was added thereto. The layers were separated and the organic layer was washed with brine and dried over magnesium sulfate. The solvent was removed in vacuo to provide the title product. This was identical with the title product obtained from procedure A.

EXAMPLE 3

6-Amino-2-(2-(4-methoxy-benzyl)-2H-[1,2,4] triazol-3-ylmethyl)-1,2,3,4-tetrahydro-isoquinoline 2-[2-(4-Methoxybenzyl)-2H-[1,2,4]triazol-3-ylmethyl]-6-nitro-1,2,3,4-tetrahydro-isoquinoline (0.5 g, 1.3 mmol) was hydrogenated in methanol (25 mL) over 10% Pd/C (0.25 g) at 50 psi (about 345 kPa) for three hours. The reaction mixture was filtered and the solvent was evaporated in vacuo. Ethyl acetate and water were added and the pH was adjusted to 10 with solid sodium carbonate. The layers were separated and the aqueous layer was extracted with additional ethyl acetate. The combined organic layers were washed with brine, dried over magnesium sulfate, filtered and evaporated in vacuo to an oil; 0.4 g, 87% yield. $^1$H NMR (CDCl$_3$) δ 7.86 (s, 1), 7.18 (d, 2), 6.79 (m, 3), 6.48 (m, 2), 5.42 (s, 2), 3.76 (s, 3), 3.73 (s, 2), 3.50 (s, 2), 2.80 (m, 2), 2.69 (m, 2). IR (KBr) 1613, 1587, 1513 cm$^{-1}$. Mass spectrum: m/z: 348 (M$^+$−1).

EXAMPLE 4

4'-Trifluoromethylbiphenyl-2-carboxylic acid [2-(2-(4-methoxybenzyl)-2H-[1,2,4]triazol-3-ylmethyl)-1,2,3,4-tetrahydroisoquinolin-6-yl]-amide The title product of Example 3 (0.38 g, 1.1 mmol) and triethylamine (0.17 mL, 1.2 mmol) were dissolved in methylene chloride (14 mL) and stirred at room temperature while a solution of 4'-trifluoromethylbiphenyl-2-carbonyl chloride (0.31 g, 1.1 mmol) in methylene chloride (40 mL) was added dropwise. After four hours, 10% aq sodium carbonate solution was added and the mixture was stirred for thirty minutes. The methylene chloride layer was washed with brine, dried over magnesium sulfate and evaporated in vacuo to afford the title product as a hard foam, 0.63 g, 97% yield. $^1$H NMR (CDCl$_3$) δ 7.79 (s, 1), 7.72 (d, 1), 7.64 (d, 2), 7.58–7.34 (m, 6), 7.12 (d, 2), 7.01 (s, 1), 6.90–6.72 (m, 4), 5.38 (s, 2), 3.73 (s, 3), 3.69 (s, 2), 3.50 (s, 2), 2.79 (t, 2), 2.68 (t, 2). IR (KBr) 1668, 1615, 1599, 1567, 1536, 1514 cm$^{-1}$. Mass spectrum: m/z: 598 (M$^+$−1).

I claim:
1. A process for preparing the compound of formula

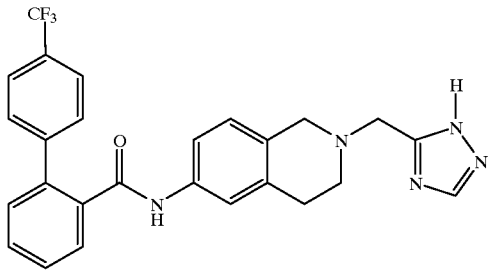

I which comprises treating the compound of the formula

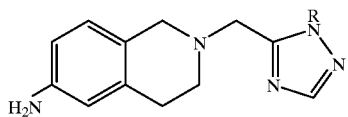

III wherein R is H or $R^2$ and $R^2$ is selected from the group comprising allyl or a substituted methyl group wherein the substituents comprise one to three $(C_6-C_{10})$aryl groups wherein the aryl groups are further optionally substituted with one or more substituents selected from nitro and $(C_1-C_6)$alkoxy;

a) with a compound of the formula

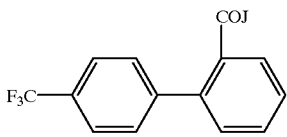

X wherein J is a leaving group such as a halogen atom, an azido group, a $(C_1-C_6)$acyloxy group or a $(C_6-C_{10})$ aroyloxy group; and b) when R is $R^2$ further treating the product of step a) with an acid.

2. The process according to claim 1 wherein said acid is selected from the group comprising trifluoroacetic acid (TFA), p-toluenesulfonic acid (PTSA), methane- or trifluoromethanesulfonic acid and HBr in acetic acid.

3. The process according to claim 2 wherein said acid is trifluoroacetic acid.

4. The process according to claim 1 wherein the compound of the formula III, wherein R is defined as above, is prepared by treating the compound of the formula

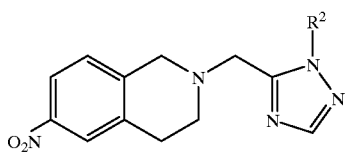

IV a) with hydrogen, in the presence of a hydrogenation catalyst, to form the compound of formula III wherein R is $R^2$; or b) 1) with an acid; and
2) treating the product of step 1) with hydrogen in the presence of a hydrogenation catalyst to form the compound of the formula III wherein R is hydrogen.

5. The process according to claim 4 wherein the compound of the formula IV is prepared by treating the compound of the formula

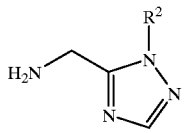

VI wherein R is $R^2$ with the compound of the formula

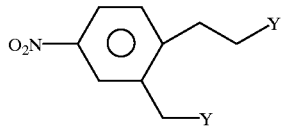

V wherein Y is as defined above, in the presence of a base.

6. A process for preparing the compound of the formula I which comprises the steps of a) preparing the compound of formula IV wherein R is $R^2$ by treating the compound of the formula VI wherein R is $R^2$ with the compound of formula V

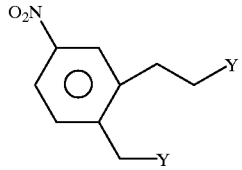

V wherein Y is as defined above, in the presence of a base;

b) treating compound IV (R=$R^2$)
1) i) with TFA to form IV (R=H);
   ii) treating IV (R=H) with hydrogen in the presence of a hydrogenation catalyst to form III (R=H); and
   iii) treating III (R=H) with X; or
2) i) with hydrogen in the presence of a hydrogenation catalyst to form III (R=$R^2$);
   ii) treating III (R=$R^2$) with X to form II (R=$R^2$); and
   iii) treating II (R=$R^2$) with TFA.

7. The process according to claim 4 wherein said hydrogenation catalyst is selected from Pd/C, Pd(OH)$_2$, Raney nickel and PtO$_2$.

8. The process according to claim 7 wherein said hydrogenation catalyst is Pd/C.

9. A compound of the formula

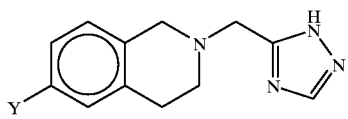

wherein Y is NH$_2$ or NO$_2$, and its tautomers.

10. The compound according to claim 9 wherein Y is NH$_2$ and its tautomers.

11. The compound according to claim 9 wherein Y is NO$_2$ and its tautomers.

12. The compound of the formula

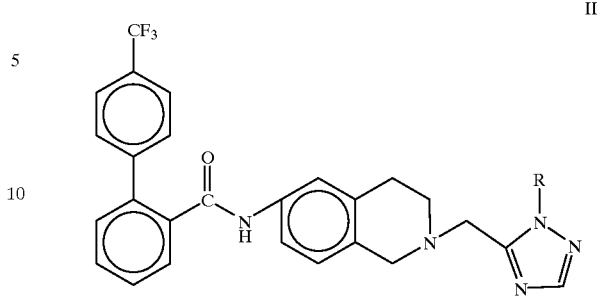

wherein R is R$^2$ and R$^2$ is selected from the group comprising allyl or a substituted methyl group wherein the substituents comprise one to three (C$_6$–C$_{10}$)aryl groups wherein the aryl groups are further optionally substituted with one or more substituents selected from nitro and (C$_1$–C$_6$)alkoxy.

13. The compound according to claim 12 wherein R$^2$ is CH$_3$OC$_6$H$_4$CH$_2$—.

* * * * *